United States Patent [19]

Pithon

[11] Patent Number: 4,620,697
[45] Date of Patent: Nov. 4, 1986

[54] SURGICAL HEADREST

[76] Inventor: Francois Pithon, 8, allee de la Mediterranee, Roanne (Loire), France

[21] Appl. No.: 679,463

[22] Filed: Dec. 7, 1984

[51] Int. Cl.$^4$ ............................................. A61G 13/00
[52] U.S. Cl. ................................................... 269/328
[58] Field of Search ..................... 269/328, 77, 78, 16; 128/1 R, 303 R, 133, 134; 5/434, 435, 436, 437, 440, 442; 108/6, 8

[56] References Cited

U.S. PATENT DOCUMENTS

| 2,507,172 | 5/1950 | Naclerio | 269/328 |
| 3,614,085 | 10/1971 | Cunningham | 269/328 |
| 4,378,108 | 3/1983 | Bailey | 269/328 |
| 4,390,011 | 6/1983 | Evans | 269/328 |
| 4,466,425 | 8/1984 | Maggi | 269/328 |

FOREIGN PATENT DOCUMENTS

| 823556 | 9/1969 | Canada | 269/328 |
| 178046 | 2/1966 | U.S.S.R. | 269/328 |

Primary Examiner—Robert C. Watson
Attorney, Agent, or Firm—Karl F. Ross; Herbert Dubno

[57] ABSTRACT

A surgical head support unit for an operating table or the like has a common support for a circular headrest which is vertically adjustable and can be tilted and a handrest for the surgeon disposed outwardly and at least partly around the headrest. The handrest for the surgeon can be adjusted independently of the headrest as to level and tilt. The support is carried by a motor-driven pair of arms which form a parallelogrammatic linkage with the support.

7 Claims, 4 Drawing Figures

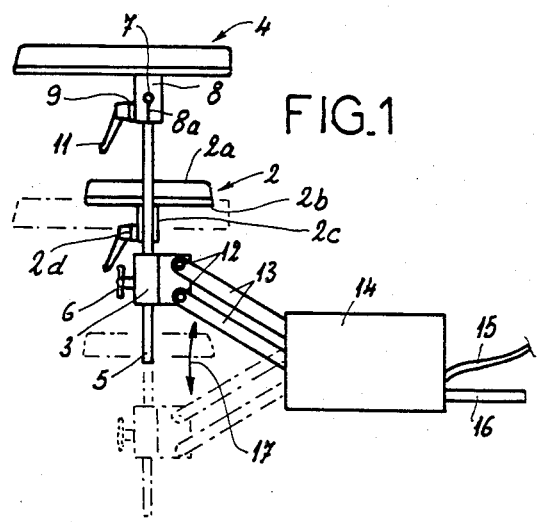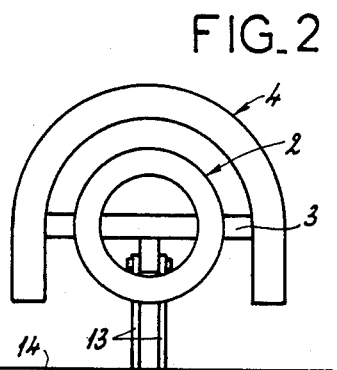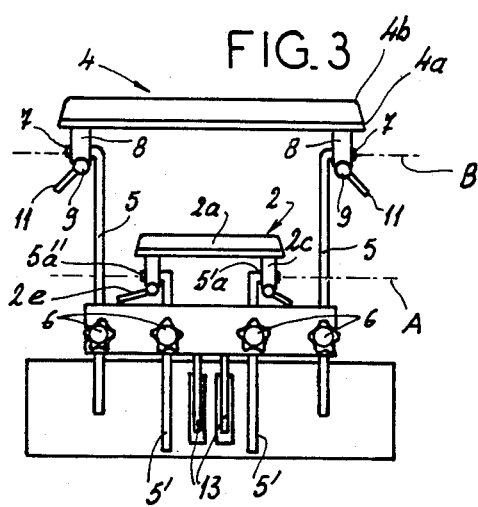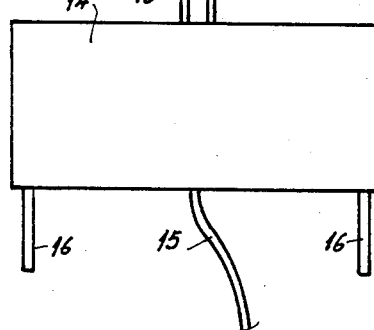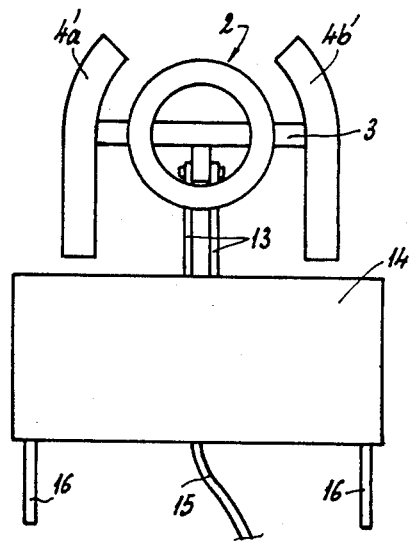

SURGICAL HEADREST

FIELD OF THE INVENTION

My present invention relates to a surgical headrest and, more particularly, to a surgical headrest of the type to be used in cranial, facial and like head surgery for supporting the head of the patient during surgical operation.

BACKGROUND OF THE INVENTION

It is known to provide surgical tables and other surgical patient supports with a headrest upon which the head of the patient can be supported during surgery. The conventional headrests utilized heretofore generally comprise a support crown which is provided with a soft and yieldable lining or cushion of foamed rubber or the like, carried by a support and provided with means enabling the level (height) of the crown and its inclination to be adjusted and fixed.

Headrests of this type have been found to be satisfactory as simple head supports for the patients but have a serious deficiency in that they are not provided or associated with any means which can form a hand or arm support for the surgeon.

In modern microsurgical techniques, in which the most delicate movements must be made or controlled by the surgeon and wherein the most delicate manipulations must be undertaken, it is absolutely imperative to provide a support for the hands of the surgeon and his assistants, as well as for the head of the patient, if accurate and effective surgery is to be carried out.

This is especially important because cranial microsurgery is itself very time consuming and tedious so that a support for the surgeon's hands or instruments may be essential not only to ensure surgical precision, but also to avoid fatigue of the surgeon.

OBJECTS OF THE INVENTION

It is the principal object of the present invention to provide a headrest which avoids the drawbacks of earlier headrests as outlined above.

Another object of this invention is to provide a surgical headrest which prevents surgeon fatigue and contributes to the accuracy of surgical manipulations and operations.

SUMMARY OF THE INVENTION

These objects and others which will become apparent hereinafter are attained, in accordance with the present invention, in a head-positioning device for surgical procedures which comprises a support, a headrest mounted on the support and inclination, a circular crown aligned with a foamed rubber or synthetic resin, and means for varying and locking the inclination and height of this headrest, which also comprises a handrest which is mounted on the same support so as to be adjustable in height (level) and inclination and to be fixed in a position of adjustment independently of the headrest, the headrest or hand support comprising a member having the configuration of at least a portion of a circular arc which is at least in part coaxial with the headrest and adapted to be disposed above or to a side of the head of the patient and adapted to be extended only limitedly around the head of the patient without masking or obscuring the head or blocking access to any part thereof at which surgical procedures may be undertaken.

The fact that the level and inclination of this member can be adjusted independently of the headrest permits the surgeon to position the handrest to his convenience in any manner so that it will best satisfy the surgeon's need for opening the skull or other incision and for carrying out the manipulations necessary to the operation.

According to a feature of the invention, the common support includes a member which is mounted for movement by a parallelopiped, the rectangular support having vertical holes in which rods or bars extending vertically at the ends of the member can slide and can be locked. A pivotal connection is formed between the ends of the member and the handrest and the pivots formed between these ends and rods can also be loosened or locked. The means for locking the rods against vertical movement can be screws threaded into a rear vertical face of the support, i.e. the most accessible face thereof. According to a specific feature of the invention, each vertical rod is formed at its upper end with a foot bent at a right angle to the balance of the rod and forming a pivot in the headrest member mentioned previously. These feet, oriented perpendicularly to the longitudinal axis of the headrest thus form pivots with respect to which the member can be locked, e.g. by clamping a bifurcated element against each leg.

In particular, the rapid locking means may include a split member in the form of a collar or ring engaging the respective foot, the opposite sides of the split being drawn together with a locking screw associated with an eccentric lever to allow rapid loosening and locking of the resulting pivot.

The configuration of the handrest or the member forming same can be that of a horseshoe or of a plurality of spaced-apart segments which can be individually adjustable.

According to a best mode embodiment of the invention, moreover, the common support is provided on a front face with two parallel horizontal axes to which are articulated the arms or levers of the parallelogrammatic linkage, an electric motor being provided to swing these levers about their respective axes to vary the level of the headrest and the surgeon's support without varying the inclinations of either of them.

BRIEF DESCRIPTION OF THE DRAWING

The above and other objects, features and advantages of the present invention will become more readily apparent from the following description, reference being made to the accompanying drawing in which:

FIG. 1 is a side elevational view in highly diagrammatic form of one embodiment of a surgeon's support associated with a surgical headrest;

FIG. 2 is a plan view of the embodiment of FIG. 1;

FIG. 3 is a rear elevational view thereof, also in highly diagrammatic form; and FIG. 4 is a plan view from above similar to FIG. 2 and illustrating a second embodiment of the invention.

SPECIFIC DESCRIPTION

As shown in FIGS. 1-3, a surgical head support unit according to the invention comprises a headrest 2 having a crown 2b surmounted by resilient and yieldable lining 2a of foamed rubber or the like, the headrest 2 having a pair of brackets 2c which can be tightened by clamps 2d upon a pair of outwardly bent pivot feet 5a' formed on the ends of a pair of rods 5. The brackets 2c are split to receive the ends 5a' so that rotation of the screws 2d by their eccentric handles 2e can tighten the screws and block inclination about a common axis A formed by the legs 5a'. The rods 5' traverse bores in a support 3 in which the rods can be clamped by screws threaded into the rear face of the support 3 and having handles 6 facilitating the tightening and loosening of these screws.

Thus relative to the support 3, the headrest 2 can be raised and lowered simply by loosening the screws of the handles 6 associated with the rods 5'. In addition, the tilt of the headrest about axis A can be set by loosening the screws associated with the handles 2e, inclining the headrest as desired and retightening these screws.

According to the invention, the support 3 additionally carries a rest 4 for the hands of the surgeon. In the embodiment of FIG. 2, this support which can include a rigid member 4a and a cushioned lining 4b is of horseshoe shape. The member 4 lies outwardly of the headrest 2 so that it can be positioned above the headrest as shown in solid lines in FIG. 1 or below the headrest as shown in dot-dash lines in this figure. In this system as well, both the level and the inclination of the handrest 4 can be adjusted and locked.

Normally as shown in FIG. 1, the member 4 is disposed to at least partly surround the head of the patient and leave accessible any portion of the head at which surgery may be required.

The means for adjusting the handrest 4 can be similar to those provided for adjusting the position and inclination of the headrest 2. In the embodiment of FIG. 4, instead of a complete horseshoe, the handrest is formed by a pair of segments 4a' and 4b' also having an arcuate configuration coaxial with the headrest. The individual elements 4a' and 4b' can be independently controllable as to inclination and height.

The common support 3 is in the form of rectangular parallelopiped which has a pair of rods 5 extending through respective bores in the support and which can be locked at any desired level by means of screws formed with the horizontal 6 as previously described and threaded into the easily accessible rear surface of the support 3. Naturally, the rods 5 may be raised and lowered to different extents if desired and certainly can be raised and lowered independently of the rods 5'.

The tilt control is effected via split collars 8 which engage bent legs 7 of the rods 5, the opposite sides of each collar 8 being drawn together or urged apart by respective screws 9 controlled by the horizontals 11. The legs 7 define a pivot axis B about which the hand support 4 can be tilted. The axis B lies in a plane perpendicular to the longitudinal axis of the headrest which corresponds generally to the longitudinal axis of the body of the patient whose head is supported by the headrest 2. The tightening of the screws 9 permits the split 8a in the bracket 8 to be closed and the leg 7 thereby clamped to lock the inclination of the handrest.

As can be seen also from FIG. 1, the common support 3 is provided with two vertically spaced horizontal axes 12 at which are articulated two support levers 13 forming a parallelogrammatic linkage and whose ends not visible in the drawing are mounted in a motor assembly 14 only the outer housing of which and the electric supply cord 15 of which are visible. The assembly may be mounted on the operating table or the like by the means represented at 16. The motor assembly is designed to swing the levers 13 in the vertical plane as illustrated by the arrow 17 and thereby raise and lower the support 3 while maintaining it parallel to itself so that the entire handrest and headrest assembly may be moved without relative adjustment from, for example, the position shown in solid lines in FIG. 1 to the dot-dash position there illustrated.

The device of the invention provides a high degree of reliability and safety during surgical operations and especially eye, ear and face microsurgery as well as in neurosurgery because the surgeon is provided with a convenient rest for his hands and his instruments, the rest being adjustable to any convenient position and orientation as may be required.

While I have illustrated two embodiments of the invention, it will be understood that other embodiments within the spirit and scope of the present claims are likewise deemed to be encompassed if the variations they represent are within the ordinary skill of the art.

I claim:

1. A surgical head support device, comprising:
   a support;
   a headrest mounted on said support and provided with means for enabling adjustment of the level and inclination of said headrest relative to said support;
   a handrest mounted on said support and extending arcuately at least in part around said headrest and substantially coaxially therewith;
   adjustment means for setting inclination and level of said handrest independently of said headrest relative to said support whereby said handrest is positionable above or below said headrest and partly surrounds the head of a patient without blocking access to portions at which surgery may be performed; and
   a motor having a pair of parallel arms extending therefrom in a vertical plane and adapted to swing said arms in said plane, said support being formed with a pair of vertically spaced parallel horizontal axes, said arms being pivotally connected to said support at said axes whereby said support is displaceable vertically parallel to itself on said arms.

2. The device defined in claim 1 wherein said support is a rectangular parallelopiped and said adjustment means includes a pair of rods extending vertically through respective bores provided in said support and means for locking said rods relative to said support.

3. The device defined in claim 2 wherein said means for locking said rods relative to said support include respective screws threaded into rear surfaces of said support, and engageable with said rods.

4. The device defined in claim 3 wherein each of said rods is provided at an upper end thereof with a leg bent at a right angle to the rod and said handrest includes at least one bracket engaging each of said legs, and means for blocking rotation of the respective bracket on the respective leg.

5. The device defined in claim 4 wherein the means for blocking rotation of the bracket relative to the respective leg includes a screw threaded into said bracket and an eccentric lever forming a horizontal cooperating with said screw.

6. The device defined in claim 5 wherein said handrest is of horseshoe shape.

7. The device defined in claim 5 wherein said handrest is provided with a plurality of independent segments.

* * * * *